US012685796B2

(12) United States Patent
Lopez-Arce et al.

(10) Patent No.: US 12,685,796 B2
(45) Date of Patent: Jul. 21, 2026

(54) DIFFERENTIAL PAIR CIRCUIT FOR EMI NOISE MITIGATION WITH UV TECHNOLOGY

(71) Applicant: Prostar Technologies Inc., Orlando, FL (US)

(72) Inventors: Rafael Lopez-Arce, Orlando, FL (US); Brenton Bailey, Maitland, FL (US)

(73) Assignee: Prostar Technologies Inc., Orlando, FL (US)

( * ) Notice: Subject to any disclaimer, the term of this patent is extended or adjusted under 35 U.S.C. 154(b) by 390 days.

(21) Appl. No.: 18/512,756

(22) Filed: Nov. 17, 2023

(65) Prior Publication Data

US 2025/0161519 A1     May 22, 2025

(51) Int. Cl.
A61L 9/20          (2006.01)

(52) U.S. Cl.
CPC ............ A61L 9/20 (2013.01); *A61L 2209/111* (2013.01); *A61L 2209/12* (2013.01)

(58) Field of Classification Search
CPC ..................................... A61L 2/10; A61L 9/20
See application file for complete search history.

(56) References Cited

U.S. PATENT DOCUMENTS 5,493,657 A     2/1996  Van Brunt et al.
2022/0362416 A1* 11/2022  Childress .................. A61L 2/10

FOREIGN PATENT DOCUMENTS

| CN | 202793464 U | 3/2013 |
|----|-------------|--------|
| CN | 210112350 U | 2/2020 |
| CN | 216902800 U | 7/2022 |
| CN | 115696689 A | 2/2023 |
| CN | 218570251 U | 3/2023 |
| CN | 116107251 A | 5/2023 |

OTHER PUBLICATIONS

Richelli, Anna, et al., "Increasing the Immunity to Eletromagnetic Interferences of CMOS OpAmps," IEEE Transactions on Reliability, vol. 52, No. 3, Sep. 2003, 5 pages.
Eadie, Ewan, et al., "Far-UVC (222 nm) efficiently inactivates an airborne pathogen in a room-sized chamber," Scientific reports, [www.nature.com/scientificreports], Mar. 2022, 9 pages.
PCA9615, "2-channel multipoint Fast-mode Plus differential I2C-bus buffer with hot-swap logic," Rev. 2, Sep. 2021, 30 pages.
English Abstract of CN Publication No. 216902800 published Jul. 5, 2022.

* cited by examiner

*Primary Examiner* — Sean E Conley
(74) *Attorney, Agent, or Firm* — Pearl Cohen LLP

(57) ABSTRACT

The disclosure relates to technology for a UV sanitization system that has an excimer ultraviolet (UV) lamp. The excimer UV lamp is configured to emit UV light into an environment in which the UV sanitization system is present. The UV sanitization system may have one or more sensors, which may be able to sense within the environment. The UV sanitization system uses differential pair communication to mitigate EMI that results from operation of the excimer UV lamp. The differential pair circuitry may include a differential communication link and fully differential operational amplifiers to process differential signals transferred over the differential communication link.

16 Claims, 11 Drawing Sheets

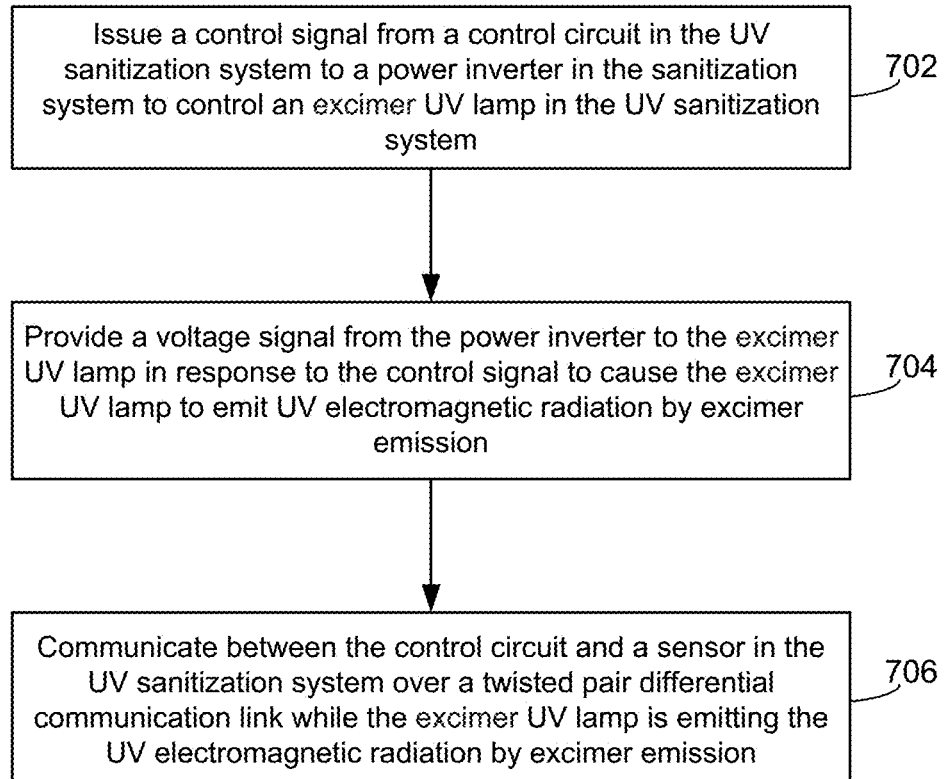

700

Issue a control signal from a control circuit in the UV sanitization system to a power inverter in the sanitization system to control an excimer UV lamp in the UV sanitization system    702

Provide a voltage signal from the power inverter to the excimer UV lamp in response to the control signal to cause the excimer UV lamp to emit UV electromagnetic radiation by excimer emission    704

Communicate between the control circuit and a sensor in the UV sanitization system over a twisted pair differential communication link while the excimer UV lamp is emitting the UV electromagnetic radiation by excimer emission    706

800

R1

R2

V+

Vout+ (Signal)

Vout- ($\overline{Signal}$)

(Signal) Vin+

$Q_1$ $Q_2$ $\overline{(Signal)}$ Vin-

R3

V-

850

R4

R5

V+

Vout+ (Signal)

Vout- ($\overline{Signal}$)

(Signal) Vin+

$M_1$ $M_2$ $\overline{(Signal)}$ Vin-

R6

V-

DIFFERENTIAL PAIR CIRCUIT FOR EMI NOISE MITIGATION WITH UV TECHNOLOGY

FIELD

The disclosure generally relates to ultraviolet (UV) sanitization.

BACKGROUND

Ultraviolet electromagnetic radiation (light) has been introduced as a means to sanitize. Ultraviolet (UV) light has been classified into at least four bands depending upon the effects upon the skin of humans and other animals. Such bands include UV-A, which is defined as ultraviolet light having a wavelength in a range from 315 nm to 400 nm; UV-B, which is defined as ultraviolet light having a wavelength in a range from 280 nm to 315 nm; UV-C, which is defined as ultraviolet light having a wavelength that is in a range from 235 nm to 280 nm; and Far UV, which is defined as ultraviolet light having a wavelength that is in a range from 185 nm to 235 nm.

Ultraviolet light in the UV-C range has been used for sanitization. For example, UV light emitted at 254 nm and 265 nm has been used to destroy viruses and other microorganisms for a number of years. Far UV light (e.g., 222 nm) has been shown to have efficacy for this use as well.

The safety of UV light to humans is dependent on the wavelength and light intensity. UV light in the UV-C range can have harmful impacts on humans. For example, prolonged direct exposure to UV-C light can result in eye and skin damage, such as acute corneal injury (sometimes referred to as "welder's eye") and acute erythema. Acute effects from UV-C light include redness, ulceration or burns of the skin. However, far-UVC is unable to penetrate the tear layer of our eyes or the dead skin layer.

Excimer lamps are capable of generating UV light in the far-UVC wavelength. The term "excimer" is short for excited dimer. Excimer lamps operate by the formation of excited dimers, which result in the emission of UV photons upon transiting from the excited state to a ground state. A typical excimer lamp contains an excimer-generating gas with the frequency of the photon depending on the type of excimer-generating gas. An example range of frequencies for light emitted from excimer lamps is 108 nm to 351 nm, depending on the excimer-generating gas.

One technique to get the excimer lamp to emit UV photons is to apply a high-voltage/high-frequency signal to the excimer lamp. A consequence of the operation of the excimer lamp is a very high amount of electromagnetic interference (EMI). This EMI presents technical challenges when operating the excimer lamp near other electronic components. One especially challenging technical issue is the corruption of data being transferred over a communication channel due to operation of a nearby excimer lamp.

BRIEF DESCRIPTION OF THE DRAWINGS

Aspects of the present disclosure are illustrated by way of example and are not limited by the accompanying figures for which like references indicate elements.

FIG. 5A is a block level diagram to illustrate an embodiment of communication over a differential amplifier pair circuit from a sensor while operating an excimer UV lamp.

FIG. 7 is a flowchart of one embodiment of a process for operating an ultraviolet (UV) sanitization system.

DETAILED DESCRIPTION

The present disclosure will now be described with reference to the figures, which in general relate to UV sanitization. An embodiment includes a UV sanitization system that has an excimer ultraviolet (UV) lamp. The excimer UV lamp is configured to emit UV light into an environment in which the UV sanitization system is present. The UV sanitization system may have one or more sensors, which may be able to sense within the environment. For example, the one or more sensors may sense $CO_2$, humidity, metal oxides, etc. The UV sanitization system may report sensor data to a client electronic device that is in wireless communication with the UV sanitization system. However, the operation of the excimer UV lamp results in a substantial amount of EMI, which can potentially corrupt data transfer within the UV sanitization system. An embodiment of the UV sanitization system uses differential pair communication to mitigate the EMI. The differential pair circuitry may include a differential communication link and fully differential operational amplifiers to process differential signals transferred over the differential communication link. Therefore, the data from the sensors may be transferred near the excimer UV lamp. Furthermore, the data from the sensors could be reported to a client electronic device that may be in wireless communication with the UV sanitization system.

It is understood that the present embodiments of the disclosure may be implemented in many different forms and that claims scopes should not be construed as being limited to the embodiments set forth herein. Rather, these embodiments are provided so that this disclosure will be thorough and complete and will fully convey the inventive embodiment concepts to those skilled in the art. Indeed, the disclosure is intended to cover alternatives, modifications and equivalents of these embodiments, which are included within the scope and spirit of the disclosure as defined by the appended claims. Furthermore, in the following detailed description of the present embodiments of the disclosure, numerous specific details are set forth in order to provide a thorough understanding. However, it will be clear to those of ordinary skill in the art that the present embodiments of the disclosure may be practiced without such specific details.

Figure 1:
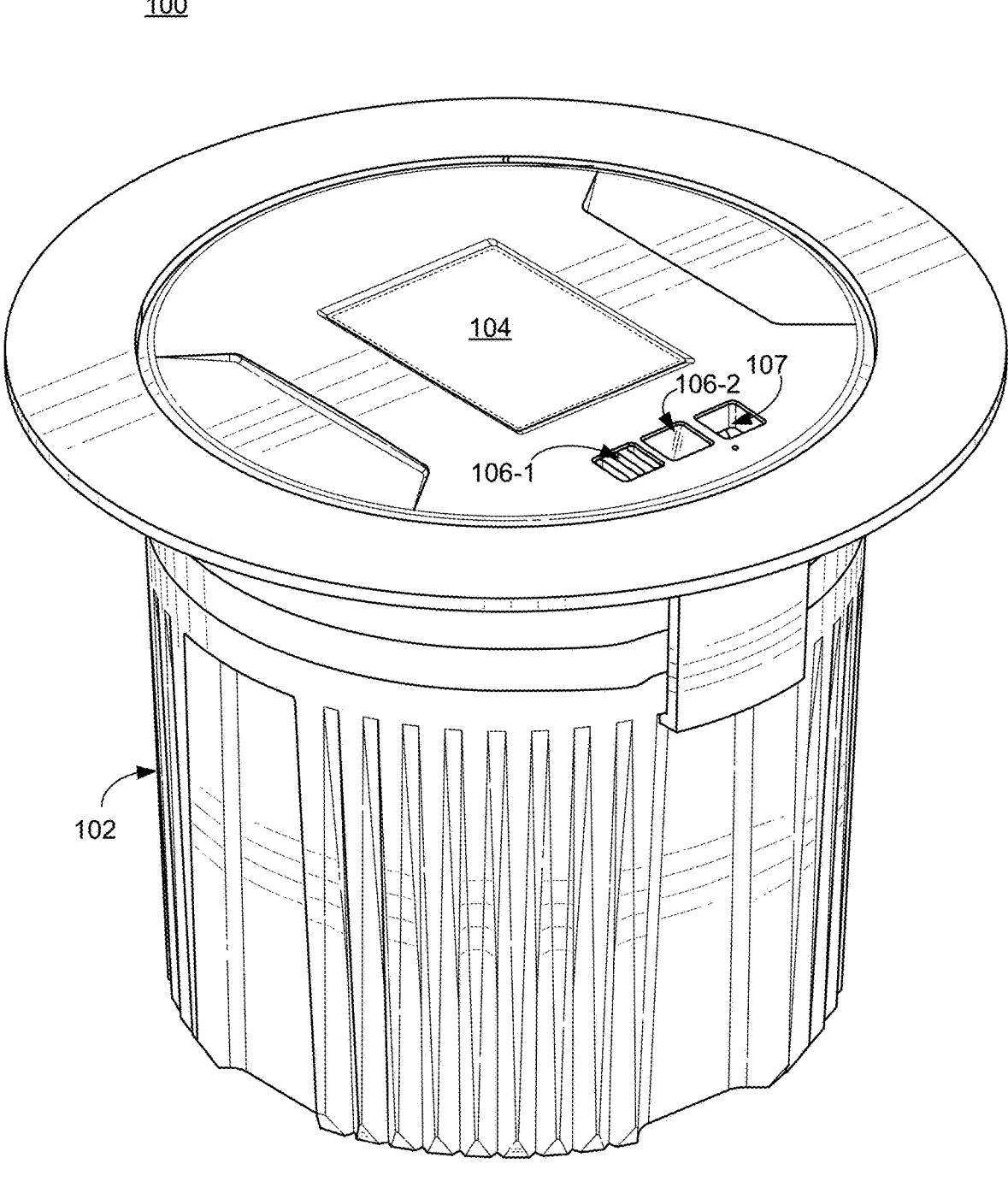
FIG. 1 illustrates one embodiment of a UV sanitization system in which embodiments may be practiced.

FIG. 1 illustrates one embodiment of a UV sanitization system 100 in which embodiments may be practiced. The UV sanitization system 100 has a housing 102 that contains various electronic circuitry. An excimer UV lamp 104 emits UV light, which may be used for sanitization. The housing 102 holds the excimer UV lamp 104 in a position to allow the excimer UV lamp 104 to emit UV light into an environment in which the UV sanitization system 100 resides. One or more sensors 106-1, 106-2 are present near the excimer UV lamp 104. The sensors 106 may be used to sense within the environment around the UV sanitization system 100. The housing 102 holds the one or more sensors 106-1, 106-2 in a position to allow the or more sensors 106-1, 106-2 to sense withing the environment in which the UV sanitization system 100 resides. In some embodiments, the sensors 106 are used to sense the air near the UV sanitization system 100. For example, carbon dioxide, humidity, air pressure, metal oxides are just a few of the things that may be sensed. Next to the sensors 106 is an LED 107. The UV sanitization system 100 may provide sensor data to a user. Therefore, sensor data may be transferred to a control circuit, or the like, which may report the sensor data to a user. Alternatively, the control circuit could use the sensor data for its own purposes without reporting the sensor data to a user. In an embodiment, the sensor data is transferred over a wired communication link within the UV sanitization system 100. The operation of the excimer UV lamp 104 may generate very high levels of EMI, which can potentially corrupt data transfer within the UV sanitization system 100. An embodiment includes the use of differential pair circuitry to mitigate EMI to therefore allow data transfer within the UV sanitization system 100.

Figure 2:
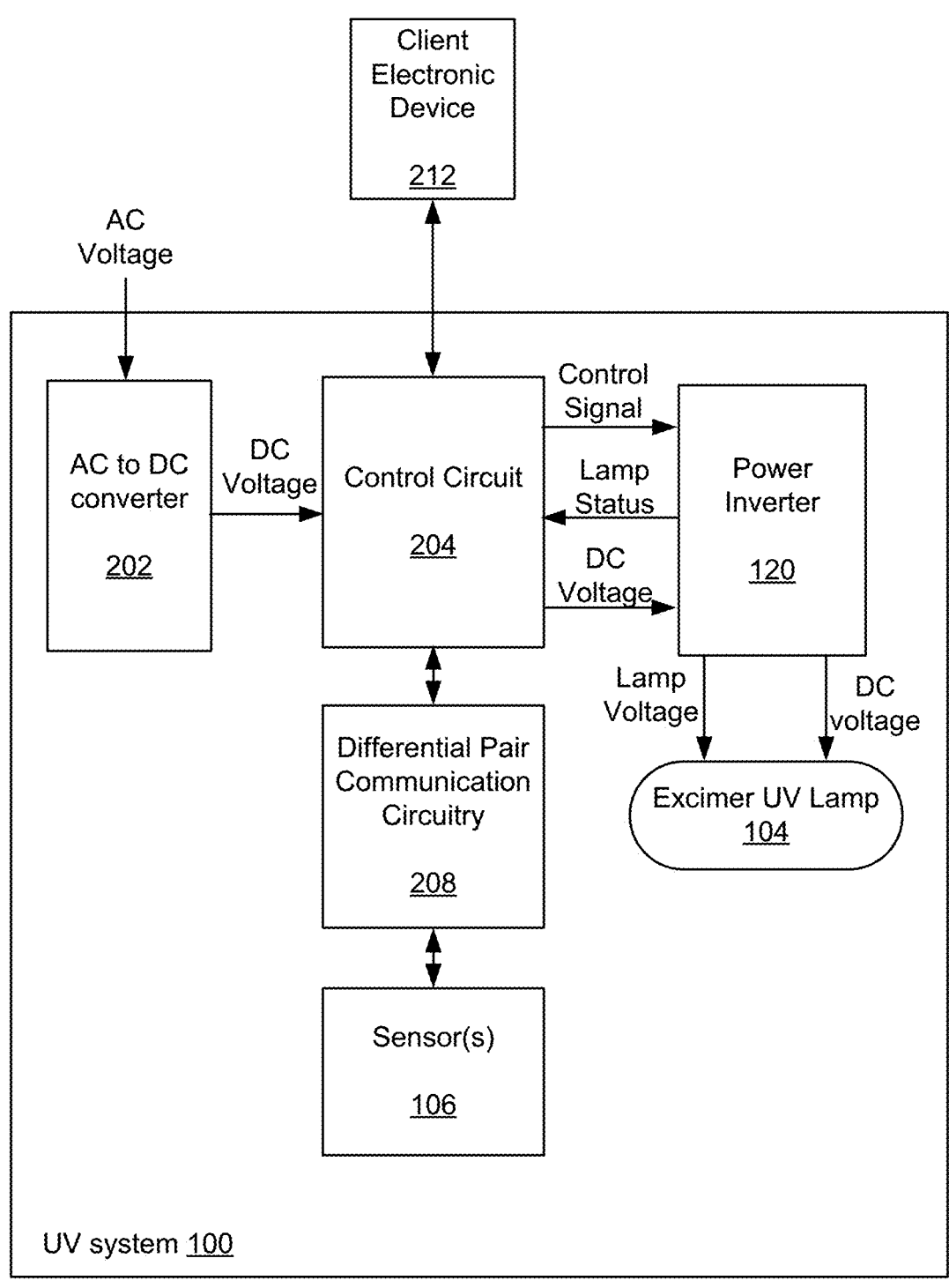
FIG. 2 is a block level diagram of one embodiment of a UV sanitization system.

FIG. 2 is a block level diagram of one embodiment of a UV sanitization system 100. FIG. 2 shows further details for one embodiment of the UV sanitization system 100 depicted in FIG. 1; however, the components in FIG. 2 may be used in a UV sanitization system 100 other than the one depicted in FIG. 1.

FIG. 2 shows that an AC (Alternating Current) to DC (Direct Current) converter 202 receives an AC voltage, which it converts to a DC voltage. As an example, the AC voltage could be a 110V AC voltage that is supplied over three lines: power, neutral, and ground. The AC voltage may be obtained from a typical AC socket in a home, office building, etc. The AC voltage is not limited to the typical voltage used in any particular region of the world. The DC voltage that is output by the AC to DC converter 202 has two lines: DC voltage and common. As one example, the DC voltage has a magnitude of 24V, but the DC voltage could be higher or lower.

The DC voltage is provided to the control circuit 204. The control circuit 204 oversees operation of the UV sanitization system 100. The control circuit 204 communicates with the sensor(s) 106 over differential pair communication circuitry 208. The control circuit 204 sends one or more control signals to the power inverter 120 to control operation of the excimer UV lamp 104. In an embodiment, the control circuit 204 sends a control signal to instruct the power inverter 120 to turn on the excimer UV lamp 104. In an embodiment, the power inverter 120 provides the present status of the excimer UV lamp 104 (e.g., whether the excimer UV lamp 104 is on or off). In an embodiment, the status of the excimer UV lamp 104 is provided on a pin that the control circuit 204 may read. The control circuit 204 may be implemented in hardware, software, or a combination of hardware and software. The control circuit 204 may include, but is not limited to, a processor (e.g., microprocessor), processor readable storage (e.g., volatile and/or non-volatile memory), a communication interface, and/or power control. The communication interface may be used to communicate with the client electronic device 212 (e.g., cellular telephone, laptop computer, notepad computer, etc.). In an embodiment, the communication interface provides for wireless communication.

The power inverter 120 converts a DC voltage to a voltage signal (e.g., Lamp Voltage) that is provided to the excimer UV lamp 104. The Lamp Voltage is a voltage signal that has a suitable voltage and a suitable frequency to cause the excimer UV lamp to emit UV light by excimer emission. The excimer UV lamp 104 contains an excimer-generating gas. Examples of excimer-generating gases include, but are not limited to, NeF, $Ar_2$, $Kr_2$, $F_2$, ArBr, $Xe_2$, ArCl, KrI, ArF, KrBr, KrCl, XeI, $Cl_2$, XeBr, $Br_2$, XeCl, $I_2$, and XeF. The frequency of the UV light that is emitted depends on the excimer-generating gas.

The Lamp Voltage is typically a high voltage. For example, the Lamp Voltage could be between about 3 kV to 6 kV, but the Lamp Voltage could be lower than 3 kV or higher than 6 kV. The Lamp Voltage typically has a high frequency. For example, the frequency of the Lamp Voltage could be between about 70 kHz to 120 kHz, but the frequency could be lower than 70 kHz or higher than 120 kHz. The Lamp Voltage may be transmitted over a first electrical line and a second electrical line that connect the excimer UV lamp 104 to the power inverter 120. The transmission of this high-voltage and/or high-frequency Lamp Voltage may generate a very substantial amount of EMI. This EMI can potentially corrupt data transmission over any wired communication links in the UV sanitization system 100.

The sensors 106 may be used to sense within the environment around the UV sanitization system 100. The sensors 106 may report data to the control circuit 204. The use of the differential pair communication circuitry 208 allows data transfer between the sensors 106 and the control circuit 204 in a noisy EMI environment that results from operation of the excimer UV lamp 104. The control circuit 204 may communicate with the client electronic device 212 to, for example, report sensor data to the client electronic device 212 and/or allow the client electronic device 212 to control the UV sanitization system 100.

Figure 3:
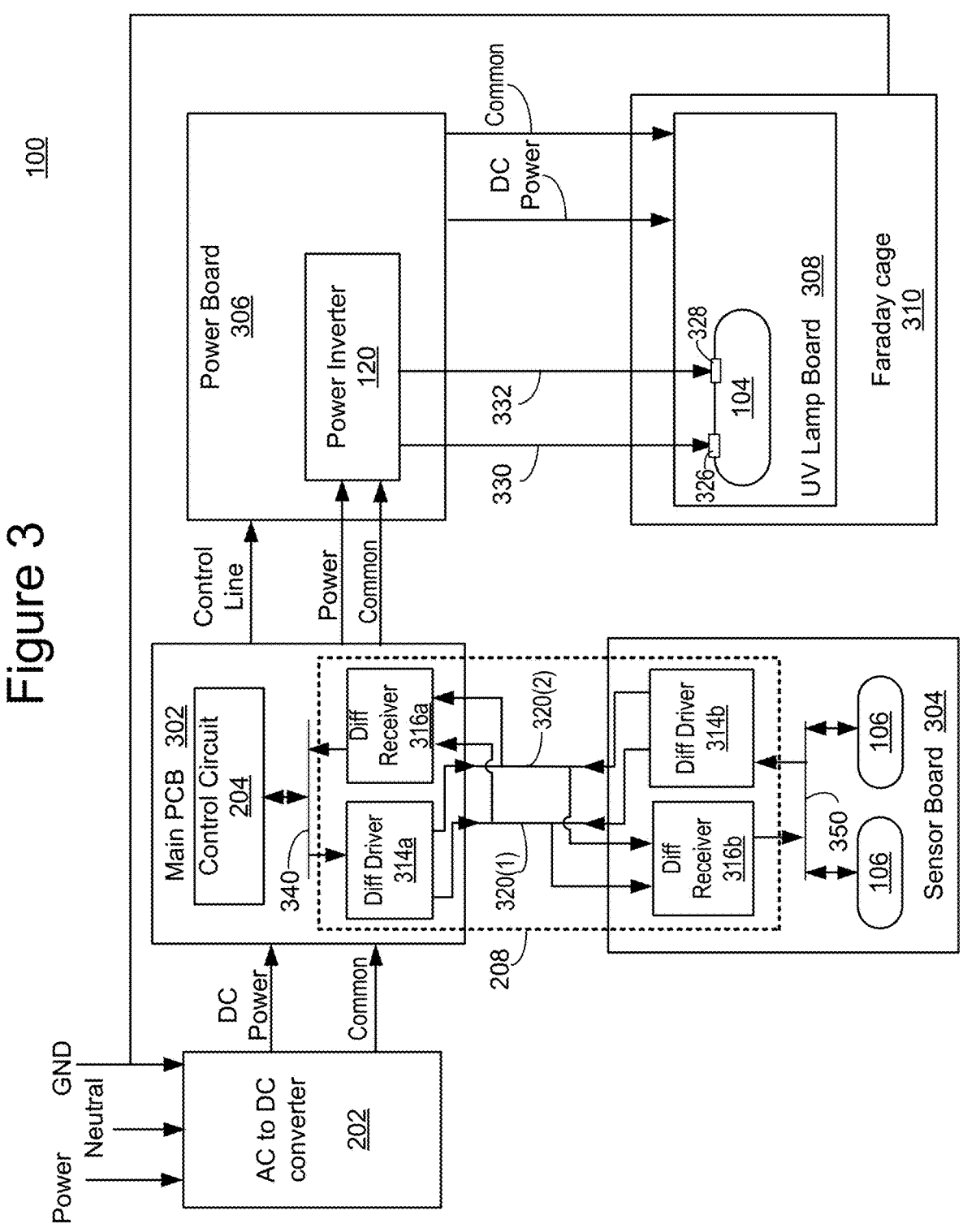
FIG. 3 is a block level diagram of one embodiment of a UV sanitization system that contains printed circuit boards.

In some embodiments, the UV sanitization system 100 contains a number of printed circuit boards on which various circuitry is mounted. FIG. 3 is a block level diagram of one embodiment of a UV sanitization system 100 that contains printed circuit boards. FIG. 3 depicts a main printed circuit board (PCB) that contains the control circuit 204 and a portion of the differential pair circuitry. In an embodiment, the main PCB 302 has a differential driver 314a that is able to drive a differential signal onto a differential communication link 320. The differential communication link has a first electrical line 320(1) and a second electrical line 320(2). In an embodiment, the first electrical line 320(1) and the second electrical line 320(2) are a twisted pair. The main PCB 302 also has a differential receiver 316a. The differential receiver 316a is connected to the differential communication link 320 to allow the differential receiver 316a to receive a differential signal from the differential communication link 320. The control circuit 204 communicates with the differential driver 314a and the differential receiver 316a over one or more busses 340. In one embodiment, the control circuit 204 uses single ended communication. The differential driver 314a and the differential receiver 316a may contain circuitry to convert between single ended and differential signals. In an embodiment, the differential receiver 316a includes a fully differential opamp that receives a differential signal from the differential communication link 320, amplifies the voltage difference at the differential input and rejects the common-mode voltage on the differential communication link 320. In an embodiment, the differential driver 314a includes a fully differential opamp to drive a differential signal onto the differential communication link 320.

A sensor PCB 304 has two sensors 106 and a portion of the differential pair circuitry. In general, the sensor PCB 304 has one or more sensors 106 that are configured to sense within the environment in which the UV sanitization system 100 resides. In an embodiment, the sensor PCB 304 has a differential driver 314b that is able to drive a differential signal onto a differential communication link 320. The sensor PCB 304 also has a differential receiver 316b. The differential receiver 316b is connected to the differential communication link 320 to allow the differential receiver 316b to receive a differential signal from the differential communication link 320. The sensors 106 communicates with the differential driver 314b and the differential receiver 316b over one or more busses 350. In one embodiment, the sensors 106 use single ended communication. The differential driver 314b and the differential receiver 316b may contain circuitry to convert between single ended and differential signals. In an embodiment, the differential receiver 316b includes a fully differential opamp that receives a differential signal from the differential communication link 320, amplifies the voltage difference at the differential input and rejects the common-mode voltage on the differential communication link 320. In an embodiment, the differential driver 314b includes a fully differential opamp to drive a differential signal onto the differential communication link 320.

The combination of the differential drivers 314, differential receivers 316, and differential electrical lines 320 collectively form at least a portion of one embodiment of the differential pair communication circuitry 208 (see FIG. 2). The arrows on the main PCB 302 and sensor PCB 304 show the direction of signal transfer. The signal transfer has been simplified for ease of illustration. The signals may include data and/or clocks. Therefore, there may be additional components such that one set of components handles data and one handles a clock.

A power board 306 contains the power inverter 120. A UV lamp board 308 contains the excimer UV lamp 104. The power inverter 120 converts a DC voltage to a lamp voltage, as has been discussed above in connection with FIG. 2. There are two electrical lines (330, 332) that connect the power inverter 120 to the excimer UV lamp 104 in order to provide the Lamp Voltage to the excimer UV lamp 104. The two electrical lines 330, 332 may be referred to as a high voltage line (V_H) and a low voltage line (V_L). The excimer UV lamp 104 has a high voltage terminal 326 connected to the high voltage electrical line 330 and a low voltage terminal connected 328 to the low voltage electrical line 332. Note that the excimer UV lamp 104 is not directly connected to either the AC ground (GND) or to the DC common. The power board 306 provides a DC voltage to the UV lamp board 308 over a DC power line and a Common line.

A faraday cage 310 surrounds the UV lamp board 308. The faraday cage 310 may also be referred to as a faraday shield. The faraday cage 310 may be formed from a conductive material. The faraday cage 310 may provide some amount of mitigation for EMI associated with operation of the excimer UV lamp 104. The faraday cage 310 is connected directly to the AC ground (GND), which improves the EMI mitigation capabilities of the faraday cage 310 to provide better mitigation for the EMI associated with operation of the excimer UV lamp 104.

Figure 4:
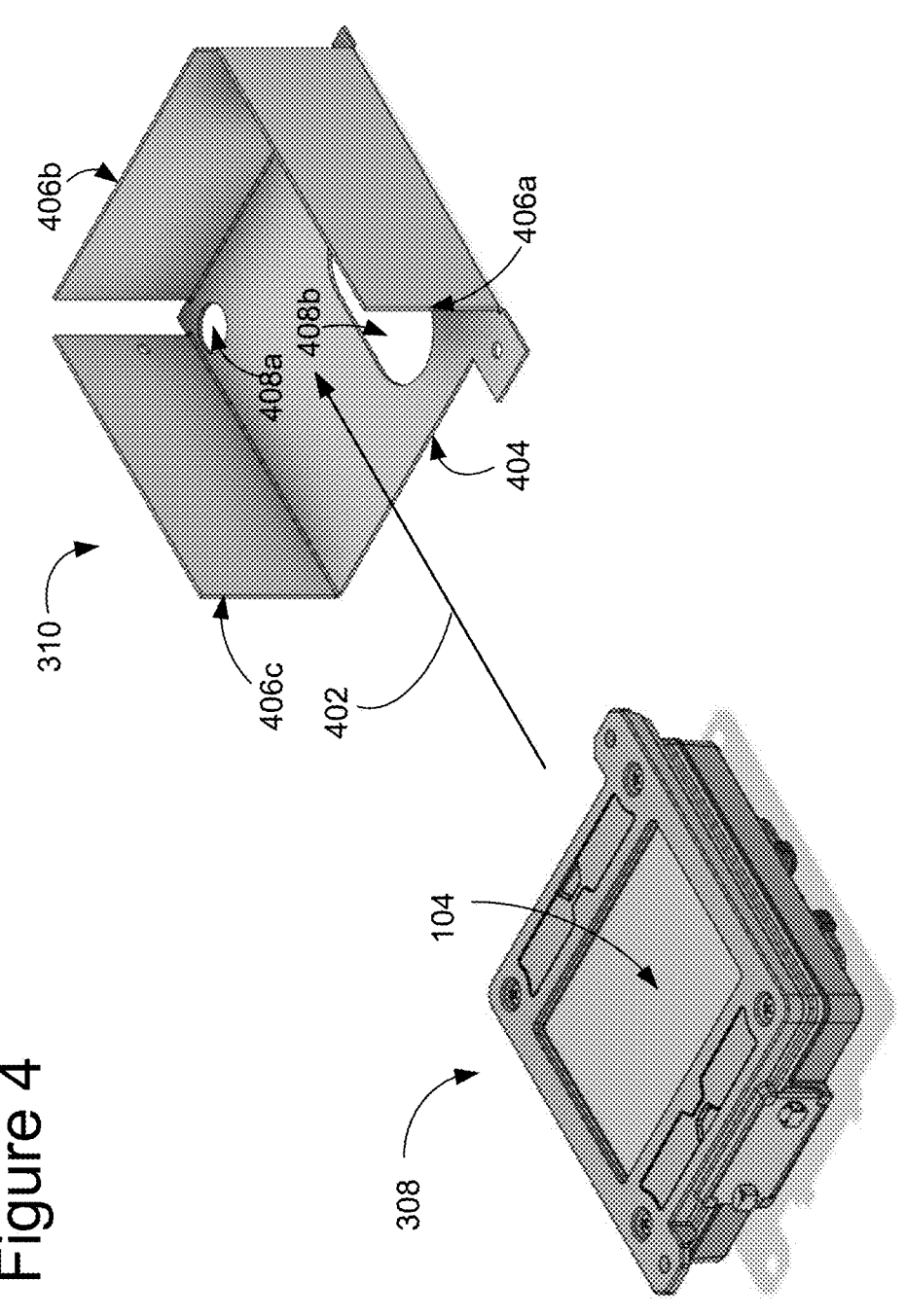
FIG. 4 illustrates how an embodiment of the UV lamp board having the excimer UV lamp may be substantially surrounded by the faraday cage.

FIG. 4 illustrates how an embodiment of the UV lamp board 308 having the excimer UV lamp 104 may be substantially surrounded by the faraday cage 310. As depicted, the UV lamp board 308 is outside the faraday cage 310. Arrow 402 shows that the UV lamp board 308 may be placed inside the faraday cage 310, while allowing for the UV light to emit from the excimer UV lamp 104. In this example, the faraday cage 310 has a bottom surface 404, and three side surfaces 406a, 406b, 406c. The bottom surface 404 may have one or more holes 408a, 408b to permit cables or the like to connect to the UV lamp board 308. The faraday cage 310 in FIG. 4 is just one example of a faraday cage 310. Other shapes and configurations may be used for the faraday cage 310.

Figure 5A:
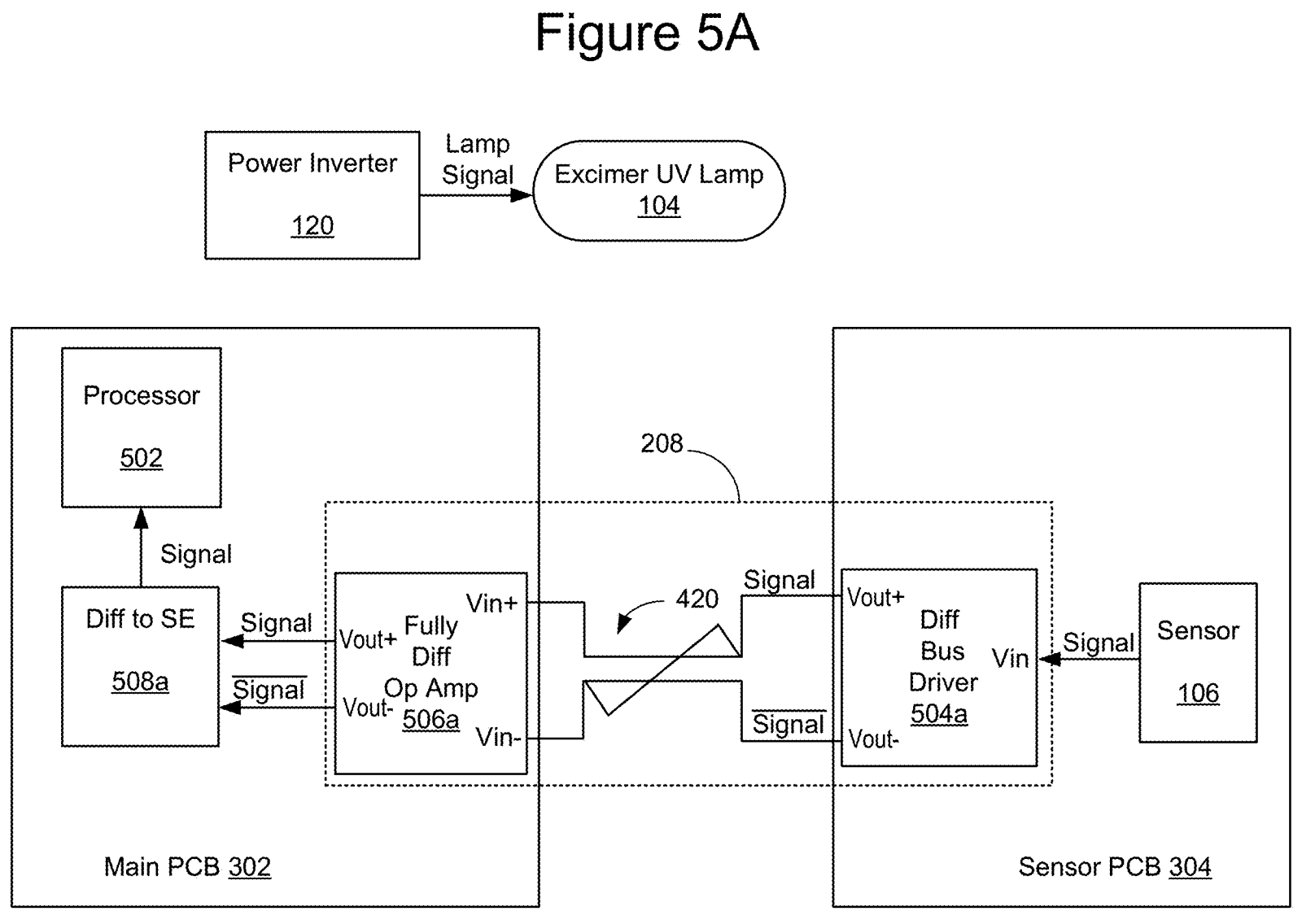
Figure 5B:
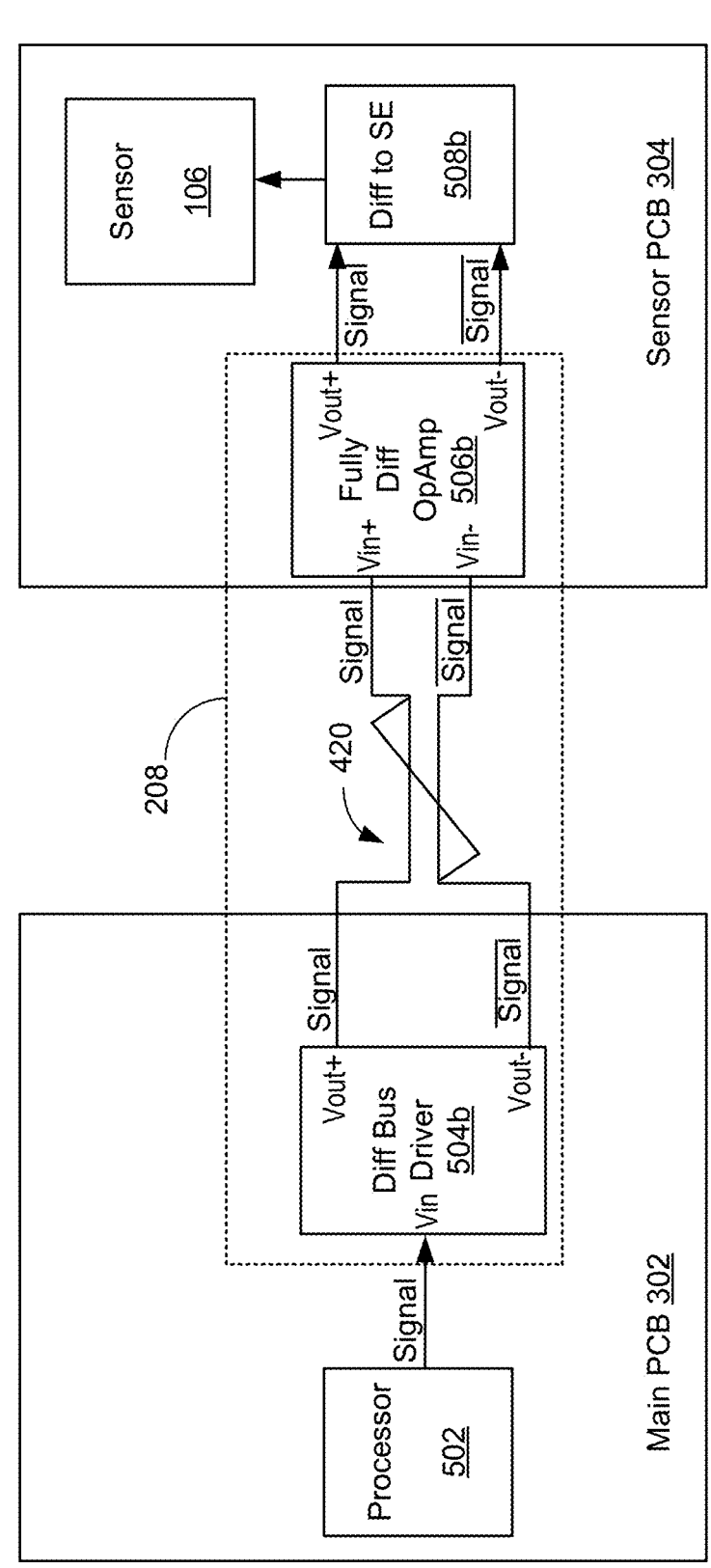
FIG. 5B is a block level diagram to illustrate an embodiment of communication over a differential amplifier pair circuit to a sensor while operating an excimer UV lamp.

FIGS. 5A and 5B are block level diagrams to illustrate further details of an embodiment of communication over a differential amplifier pair circuit while operating an excimer UV lamp. FIG. 5A depicts an embodiment of the main PCB 302, an embodiment a portion of the differential communication circuitry 208, and an embodiment of the sensor PCB 304. For the sake of discussion, FIG. 5A depicts communication of a differential signal from the sensor PCB 304 to the main PCB 302. However, differential signals may also be transferred from the main PCB 302 to the sensor PCB 304 as will be explained in connection with FIG. 5B.

The sensor PCB 304 has a sensor 106 and a differential bus driver 504a. In an embodiment, the signal from the sensor 106 is a single ended signal, which the differential bus driver 504a converts to a differential signal (Signal, Signal_Bar) at its outputs (Vout_, Vout−). Signal_Bar is the compliment of Signal. The outputs of the differential bus driver 504a are connected to the differential link 420, which in an embodiment is a twisted pair. In an embodiment, the sensor 106 and differential bus driver 504a communicate over an I2C communication link, but other communication protocols may be used.

The main PCB 302 in FIG. 5B has a processor 502 and a fully differential operational amplifier 506a. The fully differential operational amplifier 506a has a differential input (Vin+, Vin−) connected to the communication link 420 to receive the differential signal. The fully differential operational amplifier 506a may amplify the difference between its inputs and output the conditioned differential signal at its differential output (Vout+, Vout−). Thus, fully differential operational amplifier 506a amplifies the voltage difference between two inputs (Vin+, Vin) and rejects the common-mode voltage. The output signal (Vout+, Vout−) is proportional to the difference in signals between the two inputs. Note that there may be termination resistors on the main PCB 302 between the differential communication link 420 and the differential opamp 506a (termination resistors not depicted in FIG. 5A). A differential output of differential opamp 506a is connected to the differential to single ended (SE) converter 508a, which converts the differential signal to single ended and provides the single ended signal to the processor 502. In an embodiment, the diff to SE 5008a and the processor 502 communicate over an I2C communication link; however, other communication protocols may be used.

FIG. 5A also shows the power inverter 120 providing the Lamp Signal to the excimer UV lamp 104. The Lamp Voltage is a voltage signal that has a suitable voltage and a suitable frequency to cause the excimer UV lamp to emit UV light by excimer emission. The processor 502 and sensor 106 communicate using the differential communication circuitry 208 while the excimer UV lamp 104 operates. Operation of the excimer UV lamp 104 generates a substantial amount of EMI, which could potential corrupt signal transfer between the sensor 106 and processor 502. However, the use of the differential communication circuitry 208 mitigates EMI associated with operating the excimer UV lamp 104.

FIG. 5B is a block level diagram to illustrate further details of an embodiment of communication over a differential amplifier pair circuit while operating an excimer UV lamp. FIG. 5B is similar to FIG. 5A, but depicts communication of a differential signal from the main PCB 302 to the sensor PCB 304.

The main PCB 302 has processor 502 and a differential bus driver 504b. In an embodiment, the signal from the processor 502 is a single ended signal, which the differential bus driver 504b converts to a differential signal (Signal, Signal_Bar) at its outputs (Vout_, Vout−). Signal_Bar is the compliment of Signal. The outputs of the differential bus driver 504b are connected to the differential link 420, which in an embodiment is a twisted pair. In an embodiment, the processor 502 and differential bus driver 504b communicate over an I2C communication link, but other communication protocols may be used.

The sensor PCB 304 has a sensor 106 and a fully differential operational amplifier 506b. The fully differential operational amplifier 506b has a differential input (Vin+, Vin−) connected to the communication link 420 to receive the differential signal. The fully differential operational amplifier 506b may amplify the difference between its inputs and output the conditioned differential signal at its differential output (Vout+, Vout−). Thus, fully differential operational amplifier 506b amplifies the voltage difference between two inputs (Vin+, Vin) and rejects the common-mode voltage. The output signal (Vout+, Vout−) is proportional to the difference in signals between the two inputs. Note that there may be termination resistors on the sensor PCB 304 between the differential communication link 420 and the differential opamp 506b (termination resistors not depicted in FIG. 5B). A differential output of differential opamp 506b is connected to the differential to single ended (SE) converter 508b, which converts the differential signal to single ended and provides the single ended signal to the sensor 106. In an embodiment, the diff to SE 5008a and the sensor 106 communicate over an I2C communication link; however, other communication protocols may be used.

The concepts in FIGS. 5A and 5B may be combined such that each board 302, 304 contains both a differential bus driver 504 and a fully differential opamp 506 for bi-directional signal transfer. In an embodiment of bi-directional signal transfer the differential communication link 420 is shared for data transfer in each direction. For example, as depicted in FIG. 3, the diff driver 314a and the diff receiver 316a on the main PCB 302 may share the two lines 320(1), 320(2) of the differential communication link 320.

Figure 5C:
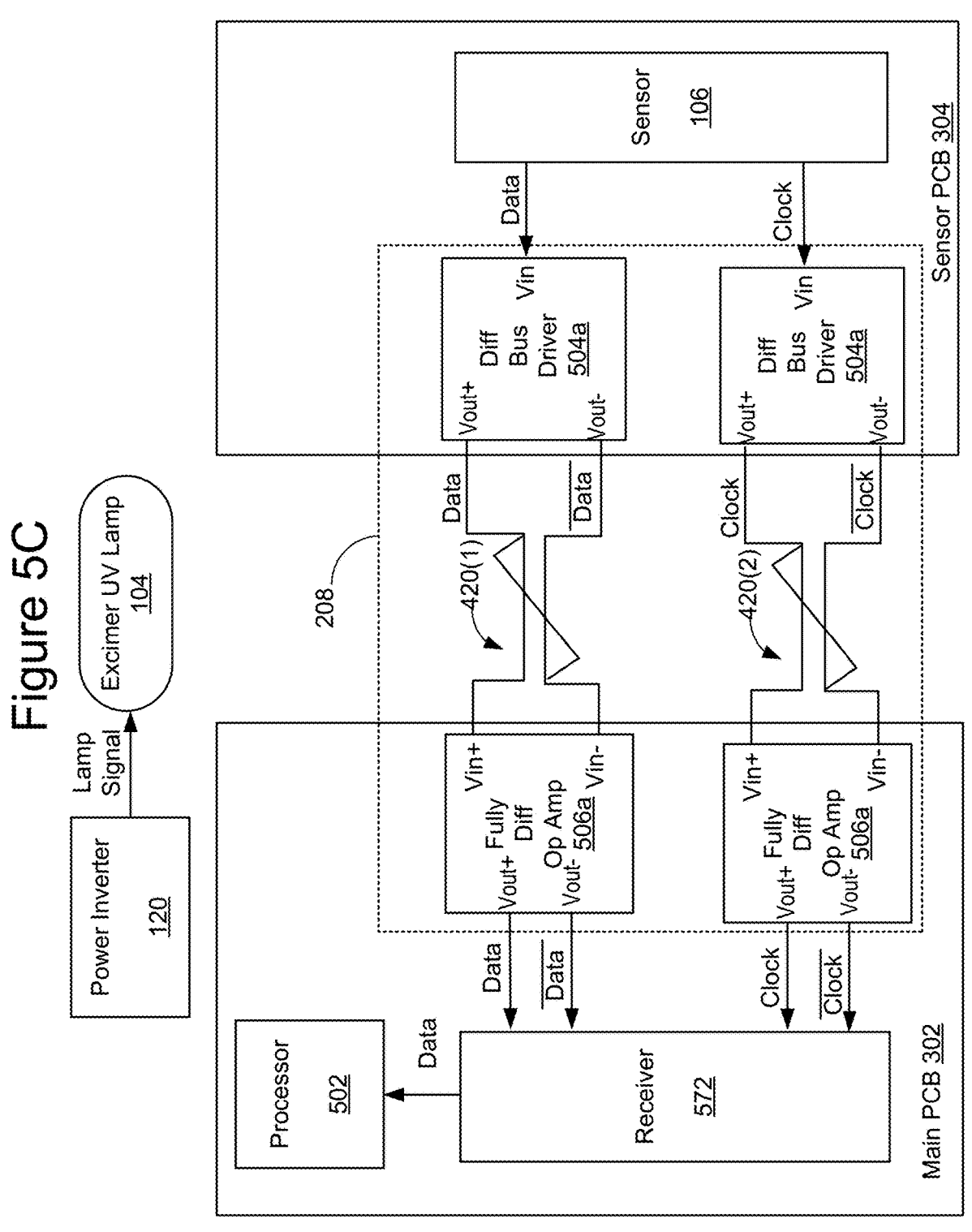
FIG. 5C depicts an embodiment in which a data signal and a clock signal are transferred from the sensor PCB to the main PCB over two different differential communication links.

Also, the differential signals in FIGS. 5A and 5B may be, for example, a clock signal (e.g., CLK, CLK_Bar) or a data signal (e.g., Data, Data_Bar). Thus, communication components depicted in FIGS. 5A and 5B may be duplicated such that both a clock signal and a data signal may be transmitted at the same time. FIG. 5C depicts an embodiment in which a data signal and a clock signal are transferred from the sensor PCB 304 to the main PCB 302 over two different differential communication links 420(1), 420(2). A receiver 572 on the main PCB 302 provides the data to the processor 502.

Figure 6A:
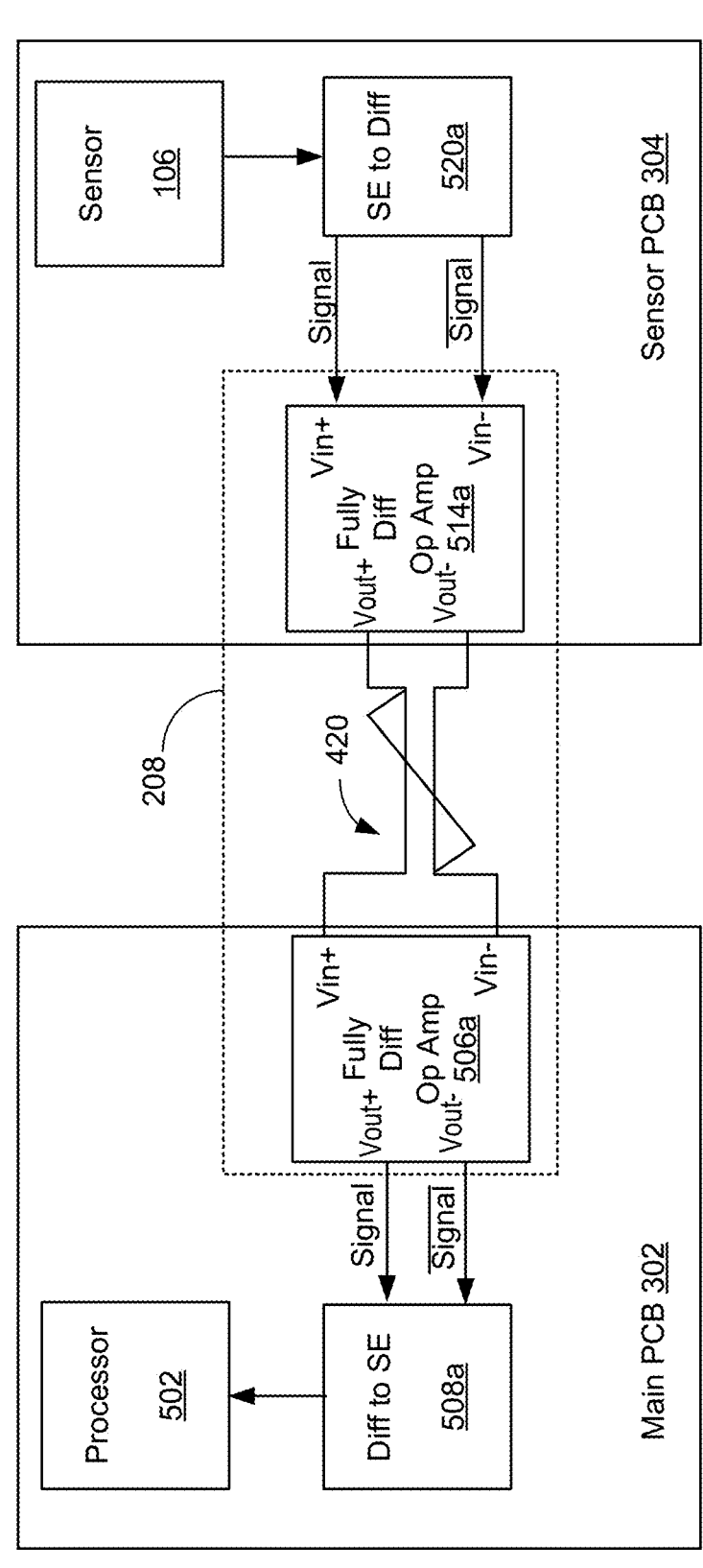
FIG. 6A is a block level diagram to illustrate an embodiment of communication over a differential amplifier pair circuit from a sensor while operating an excimer UV lamp.
Figure 6B:
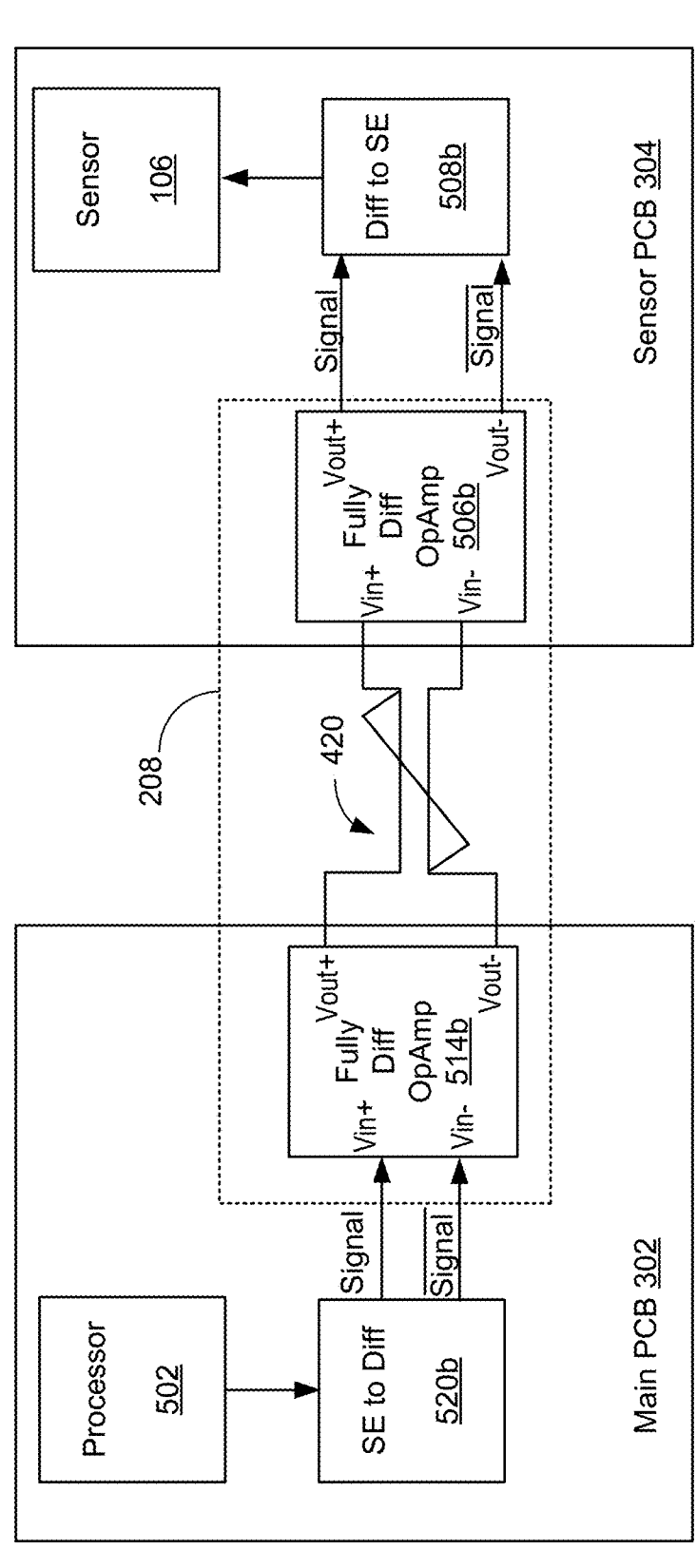
FIG. 6B is a block level diagram to illustrate an embodiment of communication over a differential amplifier pair circuit to a sensor while operating an excimer UV lamp.

FIGS. 6A and 6B are block level diagrams to illustrate further details of an embodiment of communication over a differential amplifier pair circuit while operating an excimer UV lamp. FIG. 6A depicts an embodiment of the main PCB 302, an embodiment the differential communication circuitry 208, and an embodiment of the sensor PCB 304. For the sake of discussion, FIG. 6A depicts communication of a differential signal from the sensor PCB 304 to the main PCB 302. However, differential signals may also be transferred from the main PCB 302 to the sensor PCB 304, as will be discussed with respect to FIG. 6B.

The main PCB 302 in FIG. 6A is similar to an embodiment depicted in FIG. 5A. Thus, the operation of the signal transmission on the main PCB 302 in FIG. 6A may be similar to that already discussed in connection with FIG. 5A. Therefore, the components on the main PCB 302 in FIG. 6A will not be described in detail.

The sensor PCB 304, however, has a different configuration that the sensor PCB 304 in FIG. 5A. The sensor PCB 304 has a fully differential operational amplifier 514a that receives a differential signal from a single ended (SE) to differential converter 520a. In an embodiment, the signal from the sensor 106 is a single ended signal, which the SE to diff converter 520a converts to a differential signal (Signal, Signal_Bar). Signal_Bar is the compliment of Signal. In an embodiment, the sensor 106 and the SE to diff converter 520a communicate over an I2C communication link, but other communication protocols may be used. In an embodiment, the signal from the sensor 106 is the differential signal (Signal, Signal_Bar).

The differential opamp 514a may be a fully differential opamp with a differential input (e.g., Vin_, Vin−) and a differential output (e.g., Vout+, Vout−). Opamp 514a may amplify the voltage difference between Signal and Signal_Bar and reject the common-mode voltage. The differential output of differential opamp 514a is connected to the differential communication link 420 in order to provide the differential signal (Signal, Signal_Bar) to the differential communication link 420. The differential opamp 514a is one embodiment of the differential bus driver 504a on the sensor board in FIG. 5A. However, the differential bus driver 504a on the sensor board in FIG. 5A is not limited to being a fully differential opamp.

FIG. 6A also shows the power inverter 120 providing the Lamp Signal to the excimer UV lamp 104. The Lamp Voltage is a voltage signal that has a suitable voltage and a suitable frequency to cause the excimer UV lamp to emit UV light by excimer emission. The processor 502 and sensor 106 communicate using the differential communication circuitry 208 while the excimer UV lamp 104 operates. Operation of the 104 excimer UV lamp generates a substantial amount of EMI, which could potential corrupt signal transfer between the sensor 106 and processor 502. However, the use of the differential communication circuitry 208 mitigates EMI associated with operating the excimer UV lamp 104.

FIG. 6B is a block level diagram to illustrate further details of an embodiment of communication over a differential amplifier pair circuit while operating an excimer UV lamp. FIG. 6B is similar to FIG. 6A, but depicts communication of a differential signal from the main PCB 302 to the sensor PCB 304. The sensor PCB 304 in FIG. 6B is similar to an embodiment depicted in FIG. 5B. Thus, the operation of the signal transmission on the sensor PCB 304 in FIG. 6B may be similar to that already discussed in connection with FIG. 5B. Therefore, the components on the sensor PCB 304 in FIG. 6B will not be described in detail.

The main PCB 302, however, has a different configuration that the main PCB 302 in FIG. 5B. The main PCB 302 has a fully differential operational amplifier 514*b* that receives a differential signal from a single ended (SE) to differential converter 520*b*. In an embodiment, the signal from the processor 502 is a single ended signal, which the SE to diff converter 520*b* converts to a differential signal (Signal, Signal_Bar). Signal_Bar is the compliment of Signal. In an embodiment, the processor 502 and the SE to diff converter 520*b* communicate over an I2C communication link, but other communication protocols may be used. In an embodiment, the signal from the processor 502 is the differential signal (Signal, Signal_Bar).

The differential opamp 514*b* may be a fully differential opamp with a differential input (e.g., Vin_, Vin−) and a differential output (e.g., Vout+, Vout−). Opamp 514*b* may amplify the voltage difference between Signal and Signal-_Bar and reject the common-mode voltage. The differential output of differential opamp 514*b* is connected to the differential communication link 420 in order to provide the differential signal (Signal, Signal_Bar) to the differential communication link 420. The differential opamp 514*b* is one embodiment of the differential bus driver 504*b* on the main PCB 302 in FIG. 5B. However, the differential bus driver 504*b* on the main PCB 302 is not limited to being a fully differential opamp.

The concepts in FIGS. 6A and 6B may be combined such that each board 302, 304 contains both a fully differential bus driver 514 and a fully differential receiver 506 for bi-directional signal transfer. In an embodiment of bi-directional signal transfer the differential communication link 420 is shared for data transfer in each direction. For example, as depicted in FIG. 3, the diff driver 314*a* and the diff receiver 316*a* on the main PCB 302 may share the two lines 320(1), 320(2) of the differential communication link 320. Also, the differential signals in FIGS. 6A and 6B may be, for example, a clock signal (e.g., CLK, CLK_Bar) or a data signal (e.g., Data, Data_Bar). Thus, similar as has been described above in connection with FIG. 5C, communication components depicted in FIGS. 6A and 6B may be duplicated such that both a clock signal and a data signal may be transmitted at the same time.

FIG. 7 is a flowchart of one embodiment of a process 700 for operating an ultraviolet (UV) sanitization system. Step 702 includes issuing a control signal from a control circuit 204 in the UV sanitization system 100 to a power inverter 120 in the sanitization system to control an excimer UV lamp 104 in the UV sanitization system.

Step 704 includes providing a voltage signal (e.g., Lamp Voltage) from the power inverter 120 to the excimer UV lamp 104 in response to the control signal to cause the excimer UV lamp to emit UV electromagnetic radiation by excimer emission.

Step 706 includes communicating between the control circuit 204 and a sensor 106 in the UV sanitization system 100 over a twisted pair differential communication link 420 while the excimer UV lamp is emitting the UV electromagnetic radiation by excimer emission. In an embodiment, step 706 includes driving a differential signal onto a twisted pair differential communication link 420 that includes a first electrical line 320(1) and a second electrical line 320(2) in a twisted pair configuration. The differential signal from the twisted pair differential communication link may be input into a fully differential operational amplifier 506*a*. The fully differential operational amplifier 506*a* may amplify a difference between a first voltage on the first electrical line 320(1) and a second voltage on the second electrical line 320(2). The fully differential operational amplifier 506*a* may also reject the common-mode voltage on the first electrical line 320(1) and a second voltage on the second electrical line 320(2). The amplified differential signal may be output from the fully differential operational amplifier 506*a*.

Process 700 may be used to provide sensor data to, for example, a client electronic device (see client electronic device 212 in FIG. 2). Therefore, the UV sanitization system 100 may be used to collect and report sensor data regarding the environment in which the UV sanitization system resides, as well as use the excimer UV lamp 104 to sanitize within the environment in which the UV sanitization system resides. A sensor 106 may sense within the environment in which the UV sanitization system 100 resides to produce sensor data. The sensor data may be transferred from the sensor board 304 to the main board 302 using the differential pair communication circuit 208. The control circuit 204 may transmit the sensor data to the client electronic device 212. In one embodiment, the control circuit 204 has a wireless communication interface to transmit the sensor data to the client electronic device 212.

Figures 8A, 8B:
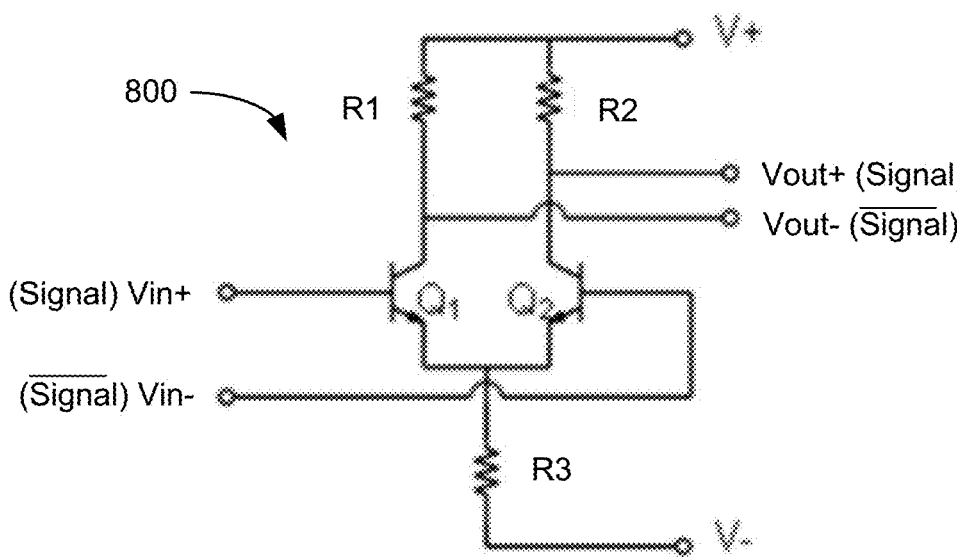
FIGS. 8A and 8B are two examples of differential opamps that may be used in the differential communication circuitry.

A wide variety of differential opamps may be used in the differential communication circuitry 208. FIGS. 8A and 8B are two examples of fully differential opamps that may be used in the differential communication circuitry 208. FIG. 8A depicts an example of a bipolar junction (BJT) differential opamp 800 that may be used in the differential communication circuitry 208. The BJT differential opamp 800 transistors Q1, Q2, and resistors R1, R2, and R3. The BJT differential opamp 800 has a differential input (Vin+, Vin−) at which a differential signal (Signal, Signal_Bar) is received. The BJT differential opamp 800 amplifies the difference between Signal and Signal_Bar and rejects the common mode voltage. The differential signal (Signal and Signal_Bar) is provided at the differential output (Vout+, Vout−).

FIG. 8B depicts an example of an MOS differential opamp 850 that may be used in the differential communication circuitry 208. The MOS differential opamp 850 has transistors M1, M2, and resistors R4, R5, and R6. The MOS differential opamp 850 has a differential input (Vin+, Vin−) at which a differential signal (Signal, Signal_Bar) is received. The MOS differential opamp 850 amplifies the difference between Signal and Signal_Bar and rejects the common mode voltage. The differential signal (Signal and Signal_Bar) is provided at the differential output (Vout+, Vout−).

Many variations of the opamps in FIGS. 8A and 8B may be used in the differential communication circuitry 208. For example, whereas the differential opamps 800, 850 have passive loads, active load differential opamps may also be used.

In view of the foregoing, an embodiment includes an apparatus comprising differential communication circuitry comprising a differential communication link having a first end and a second end. The differential communication link has a first electrical line and a second electrical line. The differential communication circuitry has a fully differential operational amplifier having a differential input connected to the first electrical line and the second electrical line at the first end of the differential communication link. The differential communication circuitry has a differential bus driver connected to the first electrical line and the second electrical line at the second end of the differential communication link. The differential bus driver is configured to drive a differential signal onto the differential communication link. The apparatus includes a control circuit in communication with a differential output the fully differential operational amplifier. The apparatus includes a sensor in communication with the differential bus driver. The control circuit is configured to communicate with the sensor with the differential signal using the differential communication circuitry. The apparatus includes an excimer ultraviolet (UV) lamp coupled to the control circuit. The control circuit is configured to control operation of the excimer UV lamp to cause the excimer UV lamp to emit UV electromagnetic radiation while the control circuit is communicating with the sensor with the differential signal using the differential communication circuitry.

In a further embodiment, the apparatus includes a power inverter configured to convert a DC voltage to a voltage signal having a voltage and a frequency suitable to cause the excimer UV lamp to generate the UV electromagnetic radiation by excimer emission. The power inverter is coupled to the excimer UV lamp to provide the voltage signal over a third electrical line and a fourth electrical line to the excimer UV lamp.

In a further embodiment, the apparatus include an AC to DC converter configured to receive an AC voltage over a power line, a neutral line, and a ground line. The AC to DC converter is configured to convert the AC voltage over the power line and the neutral line to a DC voltage. The control circuit, the sensor, and the fully differential operational amplifier are configured to operate based on DC voltages derived from the DC voltage from the AC to DC converter. And the apparatus includes a faraday cage positioned around the excimer UV lamp. The faraday cage is connected to the ground line.

In a further embodiment, the apparatus includes a printed circuit board having a DC power input having a DC power terminal and a DC common terminal. The DC power terminal and the DC common terminal are configured to receive a DC voltage derived from the DC voltage from the AC to DC converter. The excimer UV lamp is mounted on the printed circuit board. The excimer UV lamp has a high voltage terminal connected to the third electrical line and a low voltage terminal connected to the fourth electrical line.

In a further embodiment, the first electrical line and the second electrical line of the differential communication link are configured as a twisted pair.

In a further embodiment, the fully differential operational amplifier is a first fully differential operational amplifier having a first differential input connected to the first electrical line and the second electrical line at the first end of the differential communication link to process a first differential signal while the excimer UV lamp emits the UV electromagnetic radiation. The differential communication circuitry further comprises a second fully differential operational amplifier having a second differential input connected to the first electrical line and the second electrical line at the second end of the differential communication link to process a second differential signal while the excimer UV lamp emits the UV electromagnetic radiation.

In a further embodiment, the fully differential operational amplifier is a first fully differential operational amplifier. The differential bus driver comprises a second fully differential operational amplifier having a differential input connected to the first electrical line and the second electrical line at the second end of the differential communication link to drive the differential signal onto the differential communication link.

In a further embodiment, the excimer UV lamp is configured to output far UVC light while the control circuit is communicating with the sensor using the differential signal over the differential communication link.

In a further embodiment, the apparatus comprises a housing configured to house the differential communication link, the fully differential operational amplifier, and the control circuit. The housing is configured to hold the excimer UV lamp to allow the excimer UV lamp to emit the UV electromagnetic radiation into an environment in which the housing resides. The housing is configured to hold the sensor to allow the sensor to sense within the environment in which the housing resides while the excimer UV lamp is emitting the UV electromagnetic radiation into the environment by excimer emission.

In a further embodiment, the control circuit communicating with the sensor using the differential signal over the differential communication link includes transferring data about the environment from the sensor to the control circuit while the excimer UV lamp emits the UV electromagnetic radiation into the environment.

In a further embodiment, the control circuit is further configured to report the data about the environment to a client electronic device.

An embodiment includes a method for operating an ultraviolet (UV) sanitization system. The method comprises issuing a control signal from a control circuit in the UV sanitization system to a power inverter in the sanitization system to control an excimer UV lamp in the UV sanitization system. The method comprises providing a voltage signal from the power inverter to the excimer UV lamp in response to the control signal to cause the excimer UV lamp to emit UV electromagnetic radiation by excimer emission. The method comprises communicating between the control circuit and a sensor in the UV sanitization system while the excimer UV lamp is emitting the UV electromagnetic radiation by excimer emission, including: driving a differential signal onto a twisted pair differential communication link that includes a first electrical line and a second electrical line in a twisted pair configuration; inputting the differential signal from the twisted pair differential communication link into a fully differential operational amplifier; amplifying a difference between a first voltage on the first electrical line and a second voltage on the second electrical line with the fully differential operational amplifier; and outputting the amplified differential signal from the fully differential operational amplifier.

An embodiment includes an ultraviolet (UV) sanitization system. The UV sanitization system comprises differential communication circuitry having a differential communication link comprising a twisted pair of a first electrical line and a second electrical line, a first fully differential operational amplifier having a first differential input coupled to a first end of the differential communication link and a second fully differential operational amplifier having a second differential input coupled to a second end of the differential communication link. The UV sanitization system comprises a first printed circuit board having a control circuit. The control circuit is communicatively coupled with a first differential output of the first fully differential operational amplifier. The UV sanitization system comprises a second printed circuit board having a sensor. The sensor is communicatively coupled with a second differential output the second fully differential operational amplifier. The UV sanitization system comprises a third printed circuit board having a voltage inverter configured to convert a DC voltage to a voltage signal. The UV sanitization system comprises an excimer ultraviolet (UV) lamp coupled to the voltage inverter to receive the voltage signal. The control circuit is configured to control the voltage inverter to cause the voltage inverter to provide the voltage signal to the excimer UV lamp to cause the excimer UV lamp emit UVC electromagnetic radiation by excimer emission while the control circuit is communicating with the sensor with differential signals using the differential communication circuitry.

It is understood that the present subject matter may be embodied in many different forms and should not be construed as being limited to the embodiments set forth herein. Rather, these embodiments are provided so that this subject matter will be thorough and complete and will fully convey the disclosure to those skilled in the art. Indeed, the subject matter is intended to cover alternatives, modifications and equivalents of these embodiments, which are included within the scope and spirit of the subject matter as defined by the appended claims. Furthermore, in the following detailed description of the present subject matter, numerous specific details are set forth in order to provide a thorough understanding of the present subject matter. However, it will be clear to those of ordinary skill in the art that the present subject matter may be practiced without such specific details.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

The computer-readable non-transitory media includes all types of computer readable media, including magnetic storage media, optical storage media, and solid state storage media and specifically excludes signals. It should be understood that the software can be installed in and sold with the device. Alternatively the software can be obtained and loaded into the device, including obtaining the software via a disc medium or from any manner of network or distribution system, including, for example, from a server owned by the software creator or from a server not owned but used by the software creator. The software can be stored on a server for distribution over the Internet, for example.

Computer-readable storage media (medium) exclude (excludes) propagated signals per se, can be accessed by a computer and/or processor(s), and include volatile and non-volatile internal and/or external media that is removable and/or non-removable. For the computer, the various types of storage media accommodate the storage of data in any suitable digital format. It should be appreciated by those skilled in the art that other types of computer readable medium can be employed such as zip drives, solid state drives, magnetic tape, flash memory cards, flash drives, cartridges, and the like, for storing computer executable instructions for performing the novel methods (acts) of the disclosed architecture.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

For purposes of this document, each process associated with the disclosed technology may be performed continuously and by one or more computing devices. Each step in a process may be performed by the same or different computing devices as those used in other steps, and each step need not necessarily be performed by a single computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus comprising:
differential communication circuitry comprising:
a differential communication link having a first end and a second end, the differential communication link having a first electrical line and a second electrical line;
a fully differential operational amplifier having a differential input connected to the first electrical line and the second electrical line at the first end of the differential communication link; and
a differential bus driver connected to the first electrical line and the second electrical line at the second end of the differential communication link, the differential bus driver configured to drive a differential signal onto the differential communication link;
a control circuit in communication with a differential output the fully differential operational amplifier;
a sensor in communication with the differential bus driver, wherein the control circuit is configured to communicate with the sensor with the differential signal using the differential communication circuitry; and
an excimer ultraviolet (UV) lamp coupled to the control circuit, the control circuit configured to control operation of the excimer UV lamp to cause the excimer UV lamp to emit UV electromagnetic radiation while the control circuit is communicating with the sensor with the differential signal using the differential communication circuitry.

2. The apparatus of claim 1, further comprising:
a power inverter configured to convert a DC voltage to a voltage signal having a voltage and a frequency suitable to cause the excimer UV lamp to generate the UV electromagnetic radiation by excimer emission, wherein the power inverter is coupled to the excimer UV lamp to provide the voltage signal over a third electrical line and a fourth electrical line to the excimer UV lamp.

3. The apparatus of claim 1, further comprising:
an AC to DC converter configured to receive an AC voltage over a power line, a neutral line, and a ground line, the AC to DC converter configured to convert the AC voltage over the power line and the neutral line to a DC voltage, wherein the control circuit, the sensor, and the fully differential operational amplifier are configured to operate based on DC voltages derived from the DC voltage from the AC to DC converter; and a faraday cage positioned around the excimer UV lamp, wherein the faraday cage is connected to the ground line.

4. The apparatus of claim 3, further comprising:

a power inverter configured to receive the DC voltage and convert the DC voltage to a voltage signal having a voltage and a frequency suitable to cause the excimer UV lamp to generate the UV electromagnetic radiation by excimer emission, wherein the power inverter is coupled to the excimer UV lamp to provide the voltage signal over a third electrical line and a fourth electrical line to the excimer UV lamp.

5. The apparatus of claim 4, further comprising:

a printed circuit board having a DC power input having a DC power terminal and a DC common terminal, the DC power terminal and the DC common terminal configured to receive a DC voltage derived from the DC voltage from the AC to DC converter, the excimer UV lamp mounted on the printed circuit board, the excimer UV lamp having a high voltage terminal connected to the third electrical line and a low voltage terminal connected to the fourth electrical line.

6. The apparatus of claim 1, wherein the first electrical line and the second electrical line of the differential communication link are configured as a twisted pair.

7. The apparatus of claim 1, wherein the fully differential operational amplifier is a first fully differential operational amplifier having a first differential input connected to the first electrical line and the second electrical line at the first end of the differential communication link to process a first differential signal while the excimer UV lamp emits the UV electromagnetic radiation, and wherein the differential communication circuitry further comprises:

a second fully differential operational amplifier having a second differential input connected to the first electrical line and the second electrical line at the second end of the differential communication link to process a second differential signal while the excimer UV lamp emits the UV electromagnetic radiation.

8. The apparatus of claim 1, wherein the fully differential operational amplifier is a first fully differential operational amplifier and the differential bus driver comprises:

a second fully differential operational amplifier having a differential input connected to the first electrical line and the second electrical line at the second end of the differential communication link to drive the differential signal onto the differential communication link.

9. The apparatus of claim 1, wherein the excimer UV lamp is configured to output far UVC light while the control circuit is communicating with the sensor using the differential signal over the differential communication link.

10. The apparatus of claim 1, further comprising a housing configured to house the differential communication link, the fully differential operational amplifier, and the control circuit, the housing configured to hold the excimer UV lamp to allow the excimer UV lamp to emit the UV electromagnetic radiation into an environment in which the housing resides, the housing configured to hold the sensor to allow the sensor to sense within the environment in which the housing resides while the excimer UV lamp is emitting the UV electromagnetic radiation into the environment by excimer emission.

11. The apparatus of claim 10, wherein the control circuit communicating with the sensor using the differential signal over the differential communication link includes transferring data about the environment from the sensor to the control circuit while the excimer UV lamp emits the UV electromagnetic radiation into the environment.

12. The apparatus of claim 11, wherein the control circuit is further configured to report the data about the environment to a client electronic device.

13. An ultraviolet (UV) sanitization system, the UV sanitization system comprising:

differential communication circuitry having a differential communication link comprising a twisted pair of a first electrical line and a second electrical line, a first fully differential operational amplifier having a first differential input coupled to a first end of the differential communication link and a second fully differential operational amplifier having a second differential input coupled to a second end of the differential communication link;

a first printed circuit board having a control circuit, the control circuit communicatively coupled with a first differential output of the first fully differential operational amplifier;

a second printed circuit board having a sensor, the sensor communicatively coupled with a second differential output the second fully differential operational amplifier;

a third printed circuit board having a voltage inverter configured to convert a DC voltage to a voltage signal; and an excimer ultraviolet (UV) lamp coupled to the voltage inverter to receive the voltage signal, the control circuit configured to control the voltage inverter to cause the voltage inverter to provide the voltage signal to the excimer UV lamp to cause the excimer UV lamp emit UVC electromagnetic radiation by excimer emission while the control circuit is communicating with the sensor with differential signals using the differential communication circuitry.

14. The UV sanitization system of claim 13, further comprising:

an AC to DC converter configured to receive an AC voltage over a power line, a neutral line, and a ground line, the AC to DC converter configured to convert the AC voltage over the power line and the neutral line to a DC voltage, wherein the control circuit, the sensor, the first fully differential operational amplifier and the second fully differential operational amplifier are configured to operate based on DC voltages derived from the DC voltage from the AC to DC converter; and a faraday cage positioned around the excimer UV lamp, wherein the faraday cage is connected to the ground line.

15. The UV sanitization system of claim 13, further comprising:

a power inverter configured to receive a DC voltage and convert the DC voltage to the voltage signal, wherein the voltage signal has a voltage and a frequency suitable to cause the excimer UV lamp to generate the UVC electromagnetic radiation by excimer emission, wherein the power inverter is coupled to the excimer UV lamp to provide the voltage signal over a third electrical line and a fourth electrical line to the excimer UV lamp.

16. The UV sanitization system of claim 13, further comprising a housing configured to house the differential communication circuitry, the first printed circuit board, the second printed circuit board, and the third printed circuit board, wherein the housing is configured to hold the excimer UV lamp in a position to allow the excimer UV lamp to emit the UVC electromagnetic radiation into an environment in which the UV sanitization system resides, the housing configured to hold the sensor in a position to allow the sensor to sense within the environment in which the UV sanitization system resides while the excimer UV lamp emits the UVC electromagnetic radiation into the environment.

* * * * *